United States Patent
Tsuchida et al.

(10) Patent No.: US 6,916,303 B2
(45) Date of Patent: Jul. 12, 2005

(54) PHOTOREDUCTION METHOD FOR HEMOGLOBIN-VESICLE

(75) Inventors: Eishun Tsuchida, Nerima (JP); Hiromi Sakai, Nakano (JP); Hiroto Onuma, Kumamoto (JP); Shinji Takeoka, Setagaya (JP)

(73) Assignee: Japan Science and Technology Corporation, Kawaguchi (JP)

( * ) Notice: Subject to any disclaimer, the term of this patent is extended or adjusted under 35 U.S.C. 154(b) by 229 days.

(21) Appl. No.: 10/073,084

(22) Filed: Feb. 12, 2002

(65) Prior Publication Data

US 2002/0095108 A1 Jul. 18, 2002

Related U.S. Application Data

(63) Continuation of application No. PCT/JP00/09198, filed on Dec. 25, 2000.

(30) Foreign Application Priority Data

Jun. 12, 2000 (JP) ........................................ 2000-175611

(51) Int. Cl.$^7$ .............................................. A61M 37/00
(52) U.S. Cl. ..................... 604/6.09; 604/4.01; 604/6.14
(58) Field of Search ............................. 435/2; 424/533; 604/4.01, 6.01, 6.08, 500; 422/44; 436/8, 15, 66, 67

(56) References Cited

U.S. PATENT DOCUMENTS

| 4,578,056 A | | 3/1986 | King et al. | |
|---|---|---|---|---|
| 5,429,594 A | * | 7/1995 | Castle | ........................ 604/6.08 |
| 5,476,764 A | * | 12/1995 | Bitensky | ........................ 435/2 |

FOREIGN PATENT DOCUMENTS

JP  4-59735  2/1992

OTHER PUBLICATIONS

Of Sakai et al. "Physical Properties of Hemoglobin Vesicles as Red Cell Substitutes" (Biotechnol. Prog. 1996, 12, 119–125).*

Djordjevich and Miller, Lipid Encapsulated Hemoglobin as a Synthetic Erythrocyte, Federation Proceedings vol. 36, 1977.

Tsuchida ed., Perspectives of Blood Substitutes, Blood Substitutes—Present and Future Perspectives, Elsevier, Amsterdam, 1–14, 1998.

Sakai et al., Suppression of Methemoglobin Formation by Glutathione in a Concentrated Hemoglobin Solution and in a Hemoglobin–Vesicle, Bull. Chem. Soc., 67, 1120–1125, 1994.

Takeoka et al., Reduction of Methemoglobin via Electron Transfer across the Bilayer Membrane of Hb Vesicles, Bull. Chem. Soc. Jpn., 70, 1171–1178, 1997.

Vorkink et al., Photoreductionof Horse Heart Cytochrome c, Photochem. Photobiol. 19, 205–215, 1974.

Kitagawa et al., Quaternary Structure–induced Photoreduction of Haem of Haemoglobin, Nature, 281, 503–504, 1979.

(Continued)

*Primary Examiner*—Patricia Bianco
(74) *Attorney, Agent, or Firm*—Oblon, Spivak, McClelland, Maier & Neustadt, P.C.

(57) ABSTRACT

A method and an apparatus for regenerating an oxygen-binding ability by reducing the methemoglobin contained in hemoglobin-vesicle by light irradiation. This method includes adding electron donors such as amino acids, saccharides, alcohols, and/or flavin derivatives in appropriate amounts to the inner aqueous phase of the hemoglobin-vesicle, applying light to the vesicle when the content of methemoglobin increases as a result of oxidation of hemoglobin, thereby reducing the metohemoglobin. In this manner, the oxygen-binding ability is recovered, thereby maintaining the function of the hemoglobin-vesicle.

5 Claims, 1 Drawing Sheet

OTHER PUBLICATIONS

Kitagawa et al., Resonance Raman Study of Subunit Assembly Dependent Photoreduction of Heme of Extracellular Giant Hemoglobin, J. Am. Chem. Soc. 106, 1860–1862, 1984.

Morikis et al., Resonance Raman Studies of Iron Spin and Axial Coordination in Distal Pocket Mutants of Ferric Myoglobin, J. Biol. Chem. 265, 12143–12145, 1990.

Saga et al., Resonance Raman studies of oriented chromophores: Metmyoglobin single crystals, J. Chem. Phys. 90, 3015–3032, 1989.

Gu et al., Photoreduction of Heme Proteins: Spectroscopic Studies and Cross–Section Measurements, J. Am. Chem. Soc., 115, 4993–5004, 1993.

Pierre et al., One–Electron Photoreduction of Bacterial Cytochrome P–450 by Ultraviolet Light, Eur. J. BioChem. 124, 533–537, 1982.

Bazin et al., One–Electron Photoreduction of Bacterial Cytochrome P–450 by Ultraviolet Light, Eur. J. BioChem. 124, 539–544, 1982.

Yubisui et al., Stopped Flow Studies on the Nonenzymatic Reduction of Methemoglobin by Reduced Flavin Mononucleotide, J. Biol. Chem. 255, 11694–11697, 1980.

Everse, Photochemical Reductionof Methemoglobin and Methemoglobin Derivatives, Methods Enzymol. 231, 524–536, 1994.

Sakai et al., Physical Properties of Hemoglobin Vesicles as Red Cell Substitutes, Biotechnol. Progress, 12, 119–125, 1996.

Sakai et al., Surface Modification of Hemoblogin Vesicles with Poly (ethylene glycol) and Effects onAggregation, Viscosity, and Blood Flow during 90 % Exchange Transfusion in Anesthetized Rats, Bioconjugate Chem. 8, 23–30, 1997.

Ogata et al., The development of the Neo Red Cells (NRC) with enzymatic reduction system of the methemoglobin, Artificial Blood, 2, 62–66, 1994.

Sakai Hiromi et al., Photoreduction of methemoglobin by irradiation in the near–ultraviolet region, Biochemistry vol. 39, No. 47, Nov. 28, 2000, pp. 14595–14602, XP002271500, ISSN: 0006–2960.

Database WPI, Section PQ, Week 198912, Derwnt Publications Ltd., London, XP002271501, Sep. 23, 1988 and SU 1424 851 A (Transplant Artifici) (abstract).

Database WPI, Section PQ, Week 198615, Derwent Publications Ltd., London, XP002271502 (abstract) and US 4,578,056 A (EXTS) Mar. 25, 1986.

* cited by examiner

PHOTOREDUCTION METHOD FOR HEMOGLOBIN-VESICLE

CROSS REFERENCE TO RELATED APPLICATIONS

This is a Continuation Application of PCT Application No. PCT/JP00/09198, filed Dec. 25, 2000, which was not published under PCT Article 21(2) in English.

This application is based upon and claims the benefit of priority from the prior Japanese Patent Application No. 2000-175611, filed Jun. 12, 2000, the entire contents of which are incorporated herein by reference.

BACKGROUND OF THE INVENTION

1. Field of the Invention

The present invention relates to a method for regenerating the oxygen-binding ability of hemoglobin, which has been lost through oxidation, in a hemoglobin-vesicle suspension serving as an oxygen infusion (oxygen carrier), thereby maintaining its oxygen-transporting ability.

2. Description of the Related Art

The vesicle suspension including hemoglobin-vesicles can be widely used in the medical and pharmaceutical fields. In particular, the vesicular suspension, if various additives are added thereto, can be used as a blood substitute in clinical treatments.

The currently used transfusion systems for injecting human blood into a blood vessel have the following problems.

1) Infection with hepatitis and AIDS viruses may occur.
2) The storage limit of erythrocytes is 3 weeks.
3) Due to coming of aged society, the ratio of the aged patients/all patients requiring transfusion increases, whereas the total number of healthy blood donors is decreasing.
4) Contamination may occur during storage.
5) Human blood cannot be given to patients who refuse the human-blood transfusion for religious reasons.
6) The system cannot satisfy emergency needs in disaster situations.

Under these circumstances, there are great demands for an blood substitute which is available anytime and which replaces all blood types. Electrolyte transfusions and coloidal transfusions have hitherto been widely used as the blood substitution. However, these substitutes are devoid of the most important function of blood. More specifically, they do not substitute the function of erythrocytes for transporting oxygen. Hence, it has been demanded to develop a substance (oxygen transfusion) for substituting the oxygen-transporting function.

Oxygen infusion using hemoglobin (human hemoglobin, bovine hemoglobin, and recombinant hemoglobin) having an oxygen association/dissociation function have been developed. Furthermore, clinical tests have been conducted on intramolecular cross-linked hemoglobin, water-soluble polymer conjugated hemoglobin, and intermolecularly cross-linked and polymerized hemoglobin in Europe and the United States. However, it has been pointed out over time that various types of side effects are produced due to this non-cellular form of hemoglobin. Based on the clinical tests, it became apparent that the encapsulated hemoglobin, so-called cellular-type hemoglobin plays an important role.

It was found that a biologica component, phospholipid, forms the vesicle or a liposome structure by itself. In addition, Djordjevich and Miller (Fed. Proc. 36, 567, 1977) started studies on the hemoglobin-vesicle using a liposome formed of phospholipid/cholesterol/fatty acid. Since then, several groups, including the group of the present inventors, have conducted extensive studies of so called the hemoglobin-vesicle. The hemoglobin-vesicle has the following advantages.

1) It can be used as it is without modification of molecular hemoglobin.
2) Values of viscosity, colloidal osmotic pressure, and oxygen affinity can be arbitrarily adjusted.
3) Retention time in blood can be extended.
4) Various types of additives can be included in an aqueous phase within the vesicle at high concentrations.

Among these advantages, the advantage 4) is particularly important in the present invention. The present inventors originally established an efficient method for preparing the hemoglobin-vesicles. As a result, they obtained a hemoglobin-vesicles having physical properties extremely close to those of blood. The fact that the hemoglobin-vesicles transfusion has excellent oxygen transporting ability has been confirmed in animal administration tests (Tsuchida ed. Blood Substitutes Present and Future Perspectives, Elsevier, Amsterdam, 1998).

Hemoglobin contains four heme groups. When heme iron is ferrous iron ($Fe^{2+}$), oxygen can be reversibly bound to the ferrous iron. However, when the heme iron is in the oxidation state of ferric iron ($Fe^{3+}$) (called methemoglobin), oxygen cannot bind to the ferric iron. In addition, the oxygen-bound hemoglobin gradually releases a superoxide anion and changes into methemoglobin. Furthermore, the superoxide anion acts as an oxidizing agent to accelerate production of methemoglobin. In erythrocytes, there are a methemoglobin reducing system and an active oxygen removal system, which prevent the content of methemoglobin from increasing, whereas, in the hemoglobin-vesicle employing purified hemoglobin, these enzymatic systems are all eliminated in a purification step. Therefore, hemoglobin is oxidized during storage and after administration (to a body), lowering the oxygen-transfer ability. To suppress the oxidation reaction, the following methods are presently used: a method of purifying hemoglobin under mild conditions which will not inactivate the enzyme (Ogata et al. Artificial Blood 2, 62–66, 1994); a method wherein a reducing agent (glutathione, homocystine, and/or ascorbic acid) as well as an enzyme (catalase and/or superoxide dismutase) which eliminate active oxygen are added (Sakai et al., Bull, Chem, Soc. Jpn., 1994); and a method wherein metohemoglobin contained in the vesicle is reduced by adding methylene blue into the vesicle membrane, which serves as an electron transfer carrier and allows electrons transfer from NADH in the outer aqueous phase into the vesicle (Takeoka et al., Bull, Chem, Soc, Jpn, 70, 1171–1178, 1997).

On the other hand, a phenomenon where methemoglobin or cytochrome C is reduced by light irradiation has been reported, for the first time, by Vorkink and Cusanovich (Photochem. Photobiol. 19, 205–215, 1974), independently of the oxygen transfusion. In addition to this report, a phenomenon is found where a reduction reaction is also advanced by light irradiation in myoglobin and cytochrome oxidase etc. Since then, the photoreduction of a heme protein has been investigated by many biochemists (Kitagawa & Nagai, Nature, 281, 503–504, 1979; Kitagawa et al., J. Sm. Chem. Soc. 106, 1860–1862, 1984; Morikis et al., J. Biol. Chem. 265, 12143–22145, 1990; Sage et al., J. Chem. Phys. 90, 3015–3032, 1989; Gu et al., J. Am. Chem. Soc., 115, 4993–5004, 1993; Pierre et al., Eur. J. Biochem, 124, 533–537, 1982; Bazin et al., Eur. J. Biochem, 124, 539–544, 1982).

Furthermore, the following phenomenon is also known. When an oxidized flavin is added together with various types of sacrificial reagents (electron donor) to a methemoglobin solution and visible light of about 450 nm is directed to the resultant solution, a reduced-type flavin is generated, which in turn reduces methemoglobin (Yubisui et al., J. Biol. Chem. 255, 11694–11697, 1980; Everse, Methods Enzymol. 231, 524–536, 1994).

The aforementioned conventional method for reducing the oxidized-hemoglobin-vesicle has the following problems.

When blood is used as a raw material, inactivation of viruses must be primarily performed in the purification step of hemoglobin. Heating of hemoglobin is desirably performed at 60° C. for 10 hours, in the same manner as in albumin preparation. However, in the heating step, the methemoglobin-reducing enzymatic system inherently present in erythrocytes is also denatured and inactivated. The activity of the enzymatic system can be retained if the purification is performed under mild conditions, for example, in accordance with a hypo-osmotic hemolysis method. In this case, oxidation of the resultant hemoglobin-vesicle can be suppressed. However, inactivation of viruses cannot be attained. In addition, the enzymatic system is chemically labile, so that the activity of the enzymatic system decreases during storage.

Alternatively, if a relatively mild reducing agent such as glutathione or homocysteine is included in the hemoglobin-vesicle as mentioned above, heme iron previously oxidized into ferric iron is reduced into ferrous iron. Therefore, the oxidation reaction is suppressed as a whole. These reducing agents are oxidized slightly and gradually inactivated even if methemoglobin is not present. It has been therefore desired to develop a system for reducing methemoglobin to hemoglobin only when the content of methemoglobin increases.

Furthermore, as described above, it has been reported that a reduction reaction is started by applying light to a dilute methemoglobin solution, as mentioned above. However, this phenomenon occurs with an extremely low efficiency in a homogeneous solution system.

BRIEF SUMMARY OF THE INVENTION

The present invention has been made in view of the aforementioned problems. An object of the present invention is to provide a method and apparatus for regenerating the reversible oxygen binding ability of the hemoglobin-vesicles which have lost due to oxidation.

The present inventors have extensively conducted systematic studies on oxygen infusion over the years with a view of developing a method of regenerating the oxygen binding ability of the hemoglobin-vesicles, in the case where methemoglobin is produced. As a result, they arrived at the present invention by which the aforementioned problems can be solved.

More specifically, the present invention relates to a method of regenerating the oxygen binding ability of the hemoglobin-vesicle suspension serving an oxygen infusion when the oxygen binding ability is lowered. This method is characterized in that at the time hemoglobin is oxidized into methemoglobin and loses its oxygen binding ability, light is applied to a suspension containing the hemoglobin-vesicles, each of which contains an aqueous hemoglobin solution in the phospholipid vesicle and an electron donor in the inner aqueous phase thereof, thereby reducing methemoglobin into hemoglobin to regain the oxygen binding ability.

The apparatus according to the present invention is used for carrying out the method of the present invention. The apparatus comprises a blood collecting means for taking blood out of a living body after a hemoglobin-vesicle suspension defined in claim 1 is intravenously administered to the living body and then the binding ability of hemoglobin is lowered by generation of methemoglobin; an isolation means for isolating the hemoglobin-vesicles from the blood obtained by the blood collecting means; a means for applying light to the vesicle in order to regenerate the oxygen binding ability of the hemoglobin-vesicle separated; and a means for returning the hemoglobin-vesicles which has regenerated its oxygen binding ability into the living body.

DETAILED DESCRIPTION OF THE INVENTION

Figure 1:
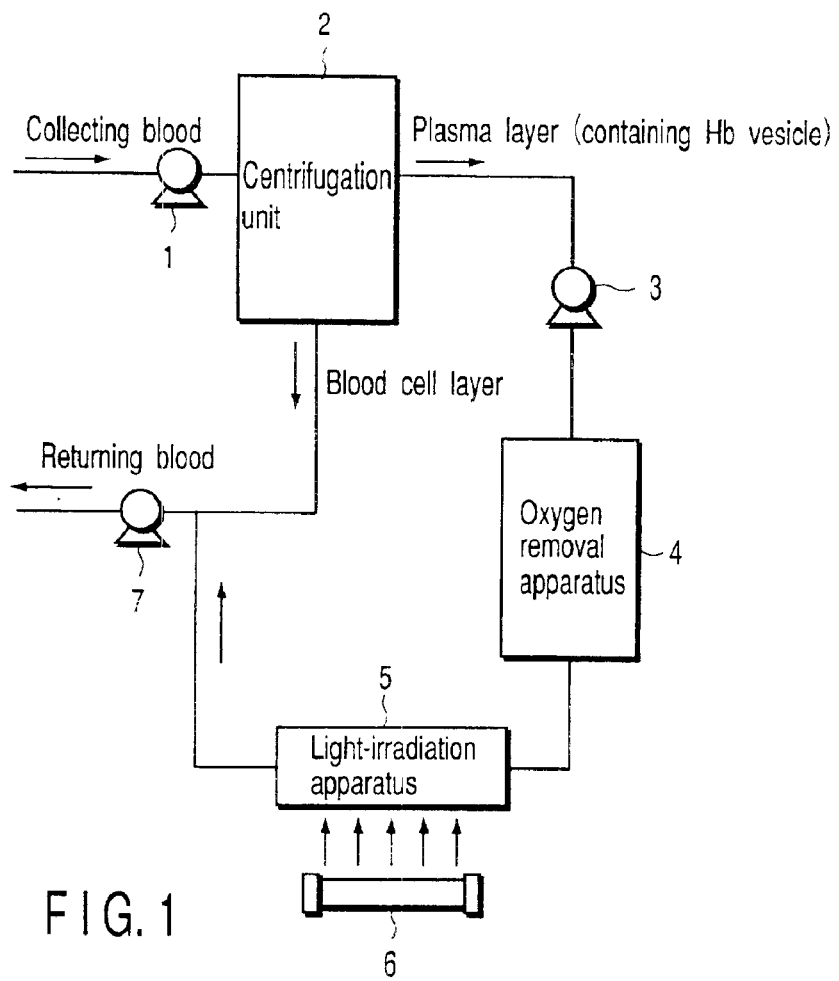
FIG. 1 is a diagram showing an embodiment of an apparatus of the present invention which is applied to an extracorporeal circulation.
Figure 2:
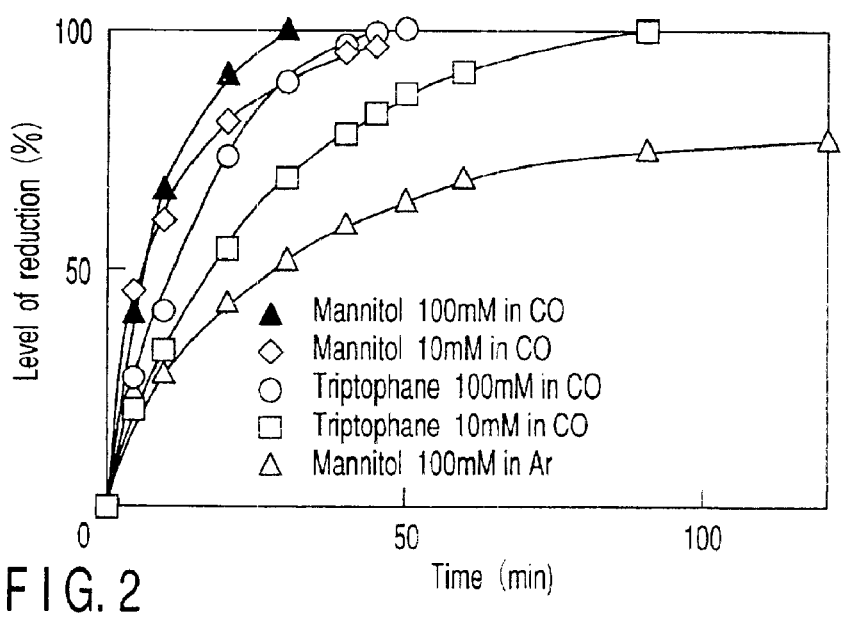
FIG. 2 is a graph showing change of reduction rates over time (the Hb concentration is 2.5 $\mu$M) in case that light of about 365 nm wave length is applied by using an extra-high pressure mercury lamp (USH-250D, Ushio Inc.) and a filter (U-360, HOYA Corporation) in combination under a carbon monoxide (CO) or Argon (Ar) atmosphere after the hemoglobin-vesicle containing mannitol or tryptophan in an amount of 10 mM or 100 mM is oxidized.

Now, the method of the present invention will be explained in detail.

The hemoglobin-vesicle of the present invention can be prepared by a method previously published by the present inventors (Sakai et al., Biotechnol. Progress, 12, 119–125, 1996; Bioconjugate Chem. 8, 23–30, 1997). The hemoglobin-vesicle, to which the present invention is applied, can be prepared in accordance with a known method except that an electron donor is previously added in a concentrated hemoglobin solution to be included in the hemoglobin-vesicle. Examples of the electron donor include substances having a hydroxyl group such as alcohols (glycerin); oxy-acid (citric acid); sugars such as mannitol, glucose, sucrose, maltose, and hyaluronic acid; and amino acids such as triptophane, tyrosine, histidine, methionine, and serine. Alternatively, as an electron mediator, a substance having an isoalloxazine ring such as flavins including flavin mononucleotide (FMN), flavin adeninedinucleotide (FAD), lumiflavin, dichlororiboflavin, riboflavin (vitamin $B_2$), and 10-methylisoalloxazine, is added in an amount of 1 $\mu$M to 100 mM. As another electron mediator, a substance serving as a light sensitizer may be used. The light sensitizer is selected from substances having a phenazine ring such as phenazine methosulfate, substances having a phenothiazine ring such as methylene blue, substances having a bipyridyl group such as ruthenium tri(2,2'-bipyridine), substances having a phenazonium ring such as cresyl blue, substances having an indigo group such as indigo sulfonic acid, substances having an indophenol ring such as 1-naphtol-2-sulfonic acid indophenol, substances such as indamines including toluylene blue, substances having an anthraquione ring such as anthraquinone-1,5-disulfoninc acid, substances having a naphtoquinone ring such as 1,2-naphthoquinone-4-sulfonic acid, substances having a benzoquinone ring, a substance having a benzoamine ring such as N,N,N,N-tetramethyl-p-phenylenediamine, substances having a carbazole group, substances having an indole ring, substances having a porphyrin ring, and the like. Incidentally, the electron mediator, when it takes the reduced form, acts as an electron donor to methemoglobin. Therefore, as the electron donor to the electron mediator, an amino acid such as methionine or cysteine; nicotine, ascorbic acid, ethylenediaminetetraacetic acid, dimethylaminopropanol, or the like, is added in an amount of 1–300 mM, together with the intermediate medium.

The present invention can be applied to the hemoglobin-vesicle obtained as described above after the hemoglobin contained therein was oxidized into methemoglobin, so that the methemoglobin is reduced into hemoglobin, thereby regenerating an oxygen binding ability thereof. The effect of the present invention can be confirmed by using, for example, suspension of hemoglobin-vesicles containing methemoglobin produced by autoxidation, or suspension of hemoglobin-vesicles containing methemoglobin, which has been oxidized by addition of sodium nitrite. To explain more specifically, the suspension is first diluted with a physiological saline solution to a predetermined concentration (e.g., hemoglobin concentration: 2.5 $\mu$M). Even if the hemoglobin-vesicle suspension is diluted herein, the concentrations of components contained in the aqueous phase within the vesicle can be maintained as they are without being diluted. This feature is quite advantageous to attaining the method of the present invention. Subsequently, the vesicle suspension is loaded into either an airtight cell formed of light-transmissible glass, plastic, or quartz; or a cell through which circulation can be established, and then, light (280–600 nm) in the range of ultraviolet/visible wavelength region is applied to the cell. At this time, in order to obtain light of a desired wavelength region, filters may be selected in combination and an appropriate laser light source may be used. In this manner, oxidized hemoglobin (methemoglobin) in the vesicle can be gradually reduced.

The method of the present invention can also be carried out as a following alternative embodiment. Specifically, after a hemoglobin-vesicle is administrated to a living body, the vesicle containing methemoglobin which has produced by oxidization within the living body is drawn out from the living body. Subsequently, photoreduction is performed to reduce the methemoglobin in to the hemoglobin for regenerating the oxygen-binding ability thereof. Thereafter, the resulting hemoglobin-vesicle is returned again into the living body. For example, in various indications such as of resuscitation fluid, hemodilution, and extracorporeal circulation in case of the hemorrhagic shock, the hemoglobin-vesicle described above can be administered into a living body. Hemoglobin contained in the vesicle is then gradually oxidized into methemoglobin to decrease an oxygen transporting ability. In such a situation, the present invention is preferably carried out as follows. Specifically, blood is partly taken out from the living body by way of a catheter, and subjected to an apparatus shown in, for example, FIG. 1.

In the apparatus of FIG. 1, blood taken by use of a catheter is sent to a centrifugal separation unit 2 by a pump 1. In the centrifugal separation unit 2, blood is separated into a blood cell component layer and a plasma layer containing the hemoglobin-vesicles. The diameters of the hemoglobin-vesicles range from 200–300 nm, which are $\frac{1}{40}$ times smaller than blood cell components. Therefore, blood cell components and the vesicles can be easily separated. As a result, the hemoglobin-vesicles can be recovered in the state of being suspended in the plasma layer. The plasma layer which includes the hemoglobin-vesicles is allowed to pass through a transparent light-emitting apparatus 5 by a pump 3. Light of a predetermined wavelength from a light source 6 is applied to the blood while the blood passes through the light-emitting apparatus; with the result that methemoglobin is reduced into hemoglobin.

As explained above, the blood cell components and the hemoglobin-vesicles are separated and only the vesicles are irradiated with the light. Therefore, hemoglobin of erythrocytes will not inhibit intended photoreduction by absorbing the light. In addition, influence of the light irradiation to the blood cell components themselves can be decreased. Furthermore, oxygen sometimes inhibits the photoreduction of the present invention. Therefore, it is preferable to remove oxygen from the solution by use of an oxygen removing apparatus 4 (for example, artificial lung). Incidentally, to increase the efficiency of light irradiation in the photoreduction reaction, it is necessary to dilute the solution to be irradiated with light and reduce the thickness of a liquid-film as thin as possible. Thus, in the light emitting apparatus 5, it is preferable that light may be applied to the light-receiving liquid while it is being circulated through a hollow fiber or by converting it into a liquid film. The plasma layer photoreduced in this manner is combined with the layer of the blood cell components which have been separated by the centrifugal separation unit 2, and then, returned into the living body by a pump 7.

As explained in the foregoing, according to the present invention, it is possible to regenerate an oxygen binding ability by applying light at the time the oxygen binding ability decreases due to oxidization of the hemoglobin-vesicles. More specifically, in the case where methemoglobin is generated after long-time storage, the methemoglobin may be reduced by light irradiation and then administered into a living body. By this approach, it is possible to utilize a maximum oxygen transferring ability of the hemoglobin-vesicles. Furthermore, when the hemoglobin-vesicles are administered into a body, the amount of methemoglobin gradually increases as the vesicles are circulated within a blood vessel. In this case, if light is applied transdermally or applied to the extracorporeal circulation passage as described above, the oxidized hemoglobin-vesicle is changed into a reduced-type hemoglobin-vesicle. As a result, the reduced-type hemoglobin-vesicle can again bind to oxygen and therefore retain a function of an oxygen infusion.

The important function of the present invention to be noted resides in that an additive serving as an electron donor and hemoglobin are contained in high concentrations in the vesicle. Consequently, reduction can be performed faster than that performed in a homogeneous solution. In addition, the reduction reaction stops upon termination of light irradiation. Therefore, the amount of electron donors consumed by oxidation (with oxygen) can be saved.

The present invention will be explained by way of examples.

EXAMPLE 1

Under a sterile atmosphere, mannitol was added to a highly purified stroma-free hemoglobin solution (40 g/dL, 6.2 mM), which was purified from human erythrocytes from donated blood, to bring final concentrations of 10 mM and 100 mM. The molar ratios of mannitol/hemoglobin of the two solutions were 1.6 and 16, respectively. The resultant solutions were filtrated by use of Remolino™ (Manufactured by Japan Millipore) with an FM micro-filter (manufactured by Fuji Photo Film Co., Ltd.) of 0.22 $\mu$m to obtain stock hemoglobin solutions. A lipid-powder mixture, Presome PPG-1, i.e., mixed lipid powder (a mixture of phosphatidylcholine/cholesterol/phosphatidyl glycerol, manufactured by Nippon Seika Co.), was added little by little to bring the concentration of lipid to 4.5 wt %. The mixture was stirred at 4° C. overnight to obtain multi-layered vesicle containing hemoglobin. At this time, the particle diameter and the number of coating lipid layers were controlled by an extrusion method using Remolino. FM micro filters having a pore diameter of 3, 0.8, 0.65, 0.45, 0.3, 0.22 μm were used in this order. After the resultant hemoglobin-vesicle solution was diluted with physiological saline and centrifugally separated (50,000 g, 40 min), the supernatant hemoglobin solution was removed under suction. Polyoxyethylene-conjugated lipid, i.e., N-(monomethoxy polyethyleneglycol-carbamyl)distearoyl phosphatidylethanolamine (the molecular weight of a polyethyleneglycol chain is 5300), was added dropwise to the mixture in an amount equal to 0.3 mol % of the lipid which was present on the outer surface of the vesicle. The reaction mixture was stirred at 25° C. for two hours and further stirred at 4° C. overnight to modify the surface of the hemoglobin-vesicle with polyethylene glycol. The concentration of hemoglobin was set at 10 g/dL. The resultant mixture was filtered by Dismic-25, 0.45 μm filter (ADVANTEC) to yield the hemoglobin-vesicle modified with polyethyleneglycol.

To the obtained hemoglobin-vesicle suspension, sodium nitrite was added to bring the concentration of methemoglobin to 100%. The vesicles were precipitated by ultracentrifugal separation and sodium nitride present in the supernatant was completely removed. Thereafter, the vesicles were dispensed with phosphate buffered saline (pH 7.4) into a quartz cell to bring the concentration of methemoglobin to 2.5 μM, and then, aerated with carbon monoxide. Subsequently, light having wavelength around 365 nm was applied by using an extra-high pressure mercury lamp (USH-250D, USHIO Inc.) and a filter (U-360, HOYA Corporation) in combination. The maximum absorption wavelength of 405 nm which is inherent to methemoglobin gradually decreased, while appeared was the maximum absorption wavelength of 419 nm which is characteristic to CO-bonded hemoglobin. This indicates that the methemoglobin-vesicles were converted into CO-bonded hemoglobin-vesicle. In the system containing 10 mM of mannitol, 60% of methemoglobin was reduced in 10 minutes, while 65% of methemoglobin was reduced in the system containing 100 mM of mannitol. The reduction reaction was completed in 50 minutes in the system containing 10 mM of mannitol, and in 30 minutes in the system containing 100 mM of mannitol. Next, when visible light was applied by use of a halogen lamp (500W) for 3 minutes under oxygen aeration, the maximum absorption wavelength changes to 415 nm. This means that the CO-bonded hemoglobin vesicle was converted into oxyhemoglobin vesicle, which contains oxygen-bonded hemoglobin.

EXAMPLE 2

The methemoglobin-vesicle (prepared in Example 1) having 100 mM mannitol in its inner aqueous phase was loaded into a quartz cell to bring the concentration of methemoglobin to 2.5 μM. Light was applied under an argon atmosphere in the same manner as mentioned in Example 1. As a result, the absorbance at the wavelength of 430 nm due to deoxyhemoglobin increased, and 80% of reduction was performed for 120 minutes. When the mixture was aerated with oxygen, an absorbance peak appeared at the wavelength of 415 nm. This observation confirmed that oxyhemoglobin (oxygen-binding hemoglobin) vesicle was produced.

COMPARATIVE EXAMPLE 1

A methemoglobin solution (in phosphate-buffered saline, pH 7.4) was prepared in a concentration of 2.5 μM. To the methemoglobin solution, mannitol was added in an amount 16 times by molar ratio compared to methemoglobin. Light reduction was performed under the same conditions as in the case of the methemoglobin-vesicle. The reduction was performed under a carbon monoxide atmosphere for 120 minutes. As a result, the reduction of methemoglobin proceeded only up to 70%. When mannitol was added in an amount of 100 mM which was 40000 times (by mole) larger than that of hemoglobin, the reduction was completed in 50 minutes. Note that the reduction did not proceed under an argon atmosphere. It turned out that the reduction efficiency performed in the methemoglobin solution is lower than that performed in the methemoglobin-vesicle, and therefore mannitol must be added in a higher concentration.

EXAMPLE 3

In the method of preparing the hemoglobin-vesicle according to Example 1, triptophane was used in place of mannitol. To be more specific, triptophane was introduced into inner-aqueous phase of hemoglobin-vesicles in an amounts of 10 mM and 100 mM in accordance with the same preparation method as in Example 1. As a result, hemoglobin-vesicles with triptophane included therein were obtained. The molar ratios of triptophane to hemoglobin used herein were 1.6 and 16, respectively. When the incubation was performed at 37° C. for 48 hours, the content of methemoglobin reached 42%. This mixture was loaded into a quartz cell to bring the concentration of methemoglobin to 2.5 μM, and then, aerated with carbon monoxide. Light having wavelength around 365 nm was applied in the same manner as in Example 1. The maximum absorption wavelength of 405 nm inherent to methemoglobin was gradually decreased, and a peak at 419 nm was increased in place. This means that methemoglobin contained in the vesicle was changed into CO-bonded hemoglobin. In the system containing 10 mM of triptophane, 33% of methemoglobin was reduced in 10 minutes, whereas 43% of the methemoglobin was reduced in the system containing 100 mM of triptophane. The reduction was completed within 90 minutes in the system containing 10 mM of triptophane, and within 50 minutes in the system containing 100 mM of triptophane. Subsequently, when the system was aerated with oxygen while applying visible light, the maximum absorption wavelength changed into 415 nm. From this observation, it was confirmed that the CO-bonded hemoglobin contained in the vesicle was converted into oxyhemoglobin, which has been bonded to oxygen.

EXAMPLE 4

The same preparation method for hemoglobin-vesicle as in Example 1 was carried out except that 5 mM of flavin mononucleotide and 200 mM of methionine were added in place of mannitol to prepare the hemoglobin-vesicle. The hemoglobin-vesicle was incubated at 37° C. for 48 hours while shielding light. As a result, the content of methemoglobin reached 40%. The resultant hemoglobin-vesicle solution was loaded into a quartz cell to bring the concentration of hemoglobin to 2.5 μM and aerated with nitrogen. Subsequently, visible light of 400–600 nm was applied by using a halogen lamp (500 W) and a filter (L-39/HA-30, HOYA Corporation) in combination. The maximum absorption at 555 nm in the Q band spectrum gradually increased, demonstrating that methemoglobin contained in the vesicle was reduced into deoxy-type hemoglobin. The reduction was completed within 5 minutes. Subsequently, when oxygen is aerated into the mixture, the peak of 555 nm in the Q band spectrum disappeared, while maximum absorption wavelengths of 541 nm and 576 nm were obtained. It was therefore demonstrated that the deoxyhemoglobin contained in the vesicle was converted into oxyhemoglobin which has been bonded to oxygen.

EXAMPLE 5

After Wistar rats (male, 300 g) were put under anesthesia by intraperitoneal injection of Nembutal. Catheters (e.g., means for taking blood) were inserted into the carotid artery and the jugular vein. A hemoglobin-vesicle suspension (hemoglobin concentration: 10 g/dL, 4 mL) added with Glucose (100 mM) was administered from the jugular vein at a speed of 1 mL/min. After 12 hours, 2 mL of blood was taken out from the carotid artery and loaded into a blood collecting tube (Terumo Corporation) having EDTA added in advance. The tube was subjected to centrifugal separation (e.g., means for isolating hemoglobin vesicles) at 2000 g for 10 minutes to obtain a hemoglobin-vesicle suspension as the supernatant. The blood-cell components of the lower layer were diluted with saline and directly administered to the rat through the jugular vein. In the hemoglobin-vesicle in the upper layer, 30% of hemoglobin was oxidized into methemoglobin. This methemoglobin vesicle was loaded into a quartz cell and bubbled (aerated) with nitrogen (e.g., means for removing oxygen). The quartz cell was irradiated with light having wavelength of about 365 nm to perform reduction (e.g., means for irradiating the hemoglobin vesicle). When deoxyhemoglobin (reduced-type hemoglobin) reached 95%, light irradiation was stopped. The deoxyhemoglobin was allowed to pass through a sterile filter of 0.45 $\mu$m pore diameter and administered to the rat through the jugular vein (e.g., means for returning the hemoglobin vesicle).

EXAMPLE 6

A mongrel dog (male, 8 kg) was put under systemic anesthesia by intramuscularly injecting ketamine hydrochloride followed by administration of Nembutal. The respiration was placed under artificial control by inserting a tube into the trachea. Ventilation capacity per breath was set at 20 mL/kg. The number of breathing was set at 12 times/min. When 240 mL of blood was allowed to breed from the femur artery, the blood pressure of the corpus artery was reduced to about 50% of the initial value. The hemoglobin-vesicle (prepared in Example 4) which contained 20 $\mu$M of flavin mononucleotide and 100 mM of methionine in an inner aqueous phase thereof was intravenously injected. As a result, the blood pressure was recovered to the same level as that before the bleeding. After 12 hours, the ratio of methemoglobin-vesicle converted from the hemoglobin-vesicle reached 40%. One hundred mL of blood was taken from the femoral artery, diluted with saline to 3 folds, and subjected to filtration by use of an ultrafilter membrane (manufactured by Millipore, mini-cassette DVPP, a nominal fraction diameter: 0.65 $\mu$m, filtration area: 0.1 m$^2$). In this manner, the blood was separated into the blood cell components and the hemoglobin-vesicles. The blood cell components were concentrated in a circulation reteutate. Immediately upon the separation, the blood cell components were intravenously injected. The filtrate, hemoglobin-vesicle containing solution was loaded into a glass container of 1L and exposed to visible light (360 W sodium lamp, manufactured by Riko Kagaku Sangyo) while stirring. After it was confirmed that the reduction rate reached 95%, light irradiation was stopped. The hemoglobin-vesicle was concentrated by an ultrafilter membrane (manufactured by Millipore, Biomax-1000, a nominal threshold molecule weight: 1000 kDa) and intravenously injected.

EXAMPLE 7

A nude rat (male, 250 g) was put under anesthesia by intraperitoneal injection of Nembutal. Catheters were inserted into the carotid artery and the jugular vein. Three mL of blood was taken out at the rate of 1 mL/min from the carotid artery to place the nude rat in the hemorrhagic shock condition. After 30 minutes, the hemoglobin-vesicle suspension (hemoglobin concentration 10 g/dL, 3 mL) containing 100 $\mu$M of the flavin mononucleotide and 100 mM of methionine in the inner aqueous phase (prepared in Example 4) was administered to the rat by way of the jugular vein at a speed of 1 mL/min. After 24 hours, 100 $\mu$L of blood was taken out from the carotid artery and the content of methemoglobin in the hemoglobin-vesicle was measured. The measurement indicated that the content of methemoglobin reached 48%. The nude rat was placed on a glass board and irradiated with visible light from both upper and lower sides by using two sodium lamps of 360W (manufactured by Riko Kagaku Sangyo), while the head was entirely covered with black cloth to prevent the eyes from being exposed to light. After the light irradiation was performed for 10 minutes, 100 $\mu$L of blood was taken out from the carotid artery and the content of methemoglobin in the hemoglobin-vesicle was measured. As a result, the content of methemoglobin decreased to 21%. From this observation, it was found that the method of the present invention is effective even if light is percutaneously applied.

What is claimed is:

1. A method of regenerating a lowered oxygen binding ability of a hemoglobin-vesicle suspension used for injection as an oxygen infusion into a blood supply, comprising:

using, as the hemoglobin-vesicle suspension, a phospholipid vesicle which includes the aqueous hemoglobin solution therein and an electron donor in an inner aqueous phase thereof; and irradiating the hemoglobin-vesicle suspension, upon withdrawal and separation of the hemoglobin-vesicle suspension from the blood supply, with light when hemoglobin in the hemoglobin-vesicle suspension is oxidized into methemoglobin and lose its oxygen biding ability, thereby reducing methemoglobin into hemoglobin to regenerate the oxygen binding ability.

2. The apparatus for carrying out the method according to claim 1, comprising:

means for taking the blood and the hemoglobin-vesicle suspension out of a living body, said taking occurring after the hemoglobin-vesicle defined in claim 1 is intravenously administered to the living body and the oxygen-binding ability of the hemoglobin-vesicle is lowered by generation of methemoglobin;

means for isolating the hemoglobin-vesicle from the blood obtained by the means for taking blood;

means for irradiating the hemoglobin-vesicle with light in order to regenerate the oxygen-binding ability of the hemoglobin-vesicle separated; and means for returning the hemoglobin-vesicle which has regenerated its oxygen-binding ability into the living body.

3. The apparatus according to claim 2, further comprising:

means for removing oxygen from the hemoglobin-vesicle isolated from the blood.

4. The method according to claim 1, wherein said electron donor is selected from the group consisting of amino acids, saccharides, alcohols and flavin derivatives.

5. The method according to claim 1, further comprising:

removing oxygen from the hemoglobin-vesicle suspension prior to the irradiating step.

* * * * *